United States Patent [19]

Montoya

[11] Patent Number: 5,698,161

[45] Date of Patent: Dec. 16, 1997

[54] HOLLOW, MULTI-DIMENSIONAL ARRAY MEMBRANE

[75] Inventor: Jean P. Montoya, Ann Arbor, Mich.

[73] Assignee: Michigan Critical Care Consultants, Inc., Ann Arbor, Mich.

[21] Appl. No.: 703,381

[22] Filed: Aug. 26, 1996

[51] Int. Cl.$^6$ .............. B01D 53/22; A61M 1/20
[52] U.S. Cl. .............. 422/48; 55/DIG. 5; 96/10; 210/321.78; 210/321.87; 210/500.23
[58] Field of Search .............. 55/DIG. 5; 96/8, 96/10, 12–14; 210/321.78, 321.79, 321.8, 321.87, 321.88, 321.89, 500.23; 422/46, 48

[56] References Cited

U.S. PATENT DOCUMENTS

| | | | |
|---|---|---|---|
| 3,445,321 | 5/1969 | Groves | 96/10 X |
| 3,794,468 | 2/1974 | Leonard | 96/10 X |
| 4,022,692 | 5/1977 | Janneck | 422/48 X |
| 4,213,858 | 7/1980 | Boberg et al. | 422/48 X |
| 4,670,313 | 6/1987 | Saudagar | 428/12 |
| 4,690,844 | 9/1987 | Saudagar | 428/36 |
| 4,911,846 | 3/1990 | Akasu et al. | 210/321.8 X |
| 5,002,666 | 3/1991 | Matsumoto et al. | 210/321.8 X |
| 5,043,140 | 8/1991 | Combs | 96/8 X |
| 5,162,101 | 11/1992 | Cosentino et al. | 422/48 X |
| 5,188,801 | 2/1993 | Fini | 96/8 X |
| 5,230,862 | 7/1993 | Berry et al. | 422/48 |
| 5,297,591 | 3/1994 | Baurmeister | 210/321.79 X |
| 5,312,589 | 5/1994 | Reeder et al. | 422/48 X |
| 5,489,413 | 2/1996 | Carson et al. | 422/48 X |
| 5,565,166 | 10/1996 | Witzko et al. | 210/321.8 X |

FOREIGN PATENT DOCUMENTS

| | | | |
|---|---|---|---|
| 3-030889 | 2/1991 | Japan | 96/10 |
| 3-135422 | 6/1991 | Japan | 96/8 |

*Primary Examiner*—Robert Spitzer
*Attorney, Agent, or Firm*—Harness, Dickey & Pierce, P.L.C.

[57] ABSTRACT

A gas permeable membrane including a plurality of conduit members which are formed of a gas permeable material. The conduit members are unitarily formed with one another and oriented to intersect one another and define a multidimensional array. Defined within each conduit member is an interior passageway and these passageways intersect and are in communication with each other. Also disclosed are methods of manufacturing the membrane and devices incorporating the membrane.

35 Claims, 6 Drawing Sheets

HOLLOW, MULTI-DIMENSIONAL ARRAY MEMBRANE

BACKGROUND OF THE INVENTION

1. Field of the Invention

The invention generally relates to gas permeable membranes and more specifically to a hollow, multi-dimensional array membrane. A membrane according to the principles of the present invention will find utility in numerous applications, including blood oxygenators, mass transfer, and energy transfer across membranes.

2. Description of the Prior Art

Currently, gas dissolution into a fluid, such as oxygen into blood, is performed either by direct contact of the gas with the fluid or by permeation of the gas across a membrane and into the fluid. Gas dissolution and permeation is often required in many different fields of endeavor and often in many different applications or situations within those fields. In the medical context, one such application and situation is blood oxygenation during cardiopulmonary bypass (CPB) surgery. For the sake of clarity, the present invention will be described in this context. It should be understood, however, that no such limitation is intended to be placed on the present invention and that the scope of this invention is intended to be within the full range of applications with which the invention may be utilized, now known or yet to be appreciated.

Previously, blood oxygenation has been performed by bubble oxygenators, solid silicone membranes and microporous membrane hollow fibers (MMHF).

With the advent of highly efficient MMHFs, many manufacturers of blood oxygenators for CPB surgery have shifted from producing bubble oxygenators and solid silicone membrane oxygenators to compact MMHF oxygenators. The advantages of the MMHF oxygenators over these other devices were significant, mainly seen in gas exchange performance and reduced blood trauma associated with the direct blood-oxygen contact.

As a result of the enhanced performance characteristics, MMHF's have become standard in blood oxygenating devices which are used for short term cardiorespiratory support procedures (e.g., routine bypass operations of about four hours). The increased gas exchange performance of these devices is principally due to the convective mixing which is induced as the blood flows over the outside of the thousands of tiny hollow fibers, within which the gas flows, resulting in the downstream fibers being situated in a mixed flow or wake generated by the upstream fibers. Capitalizing on this mixing effect, highly efficient gas exchange devices can be designed in relatively compact volumes.

Figure 1:
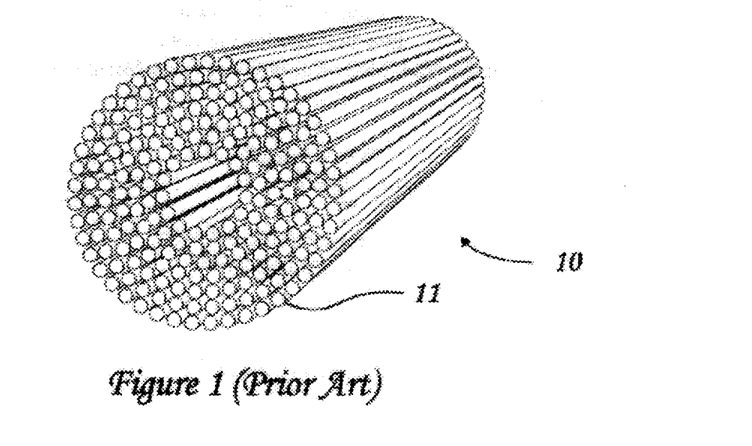
FIG. 1 is an enlarged perspective view of a prior art MMHF bundle with a parallel weave orientation.

The MMHF devices are typically constructed by winding a MMHF (supplied in a spool format from the manufacturer) into a fiber bundle, with the desired weaving pattern among fibers. FIG. 1 illustrates a prototypical concentrically wound, fiber bundle 10 with the fibers 11 oriented in a parallel pattern. Typically, the diameters of the fibers 11 are between 0.010 to 0.015 inches. Another known weaving pattern provides the MMHFs in a crisscrossed pattern so that fibers 11 in successive or contiguous layers only contact at intersecting points, rather than longitudinally along the length of the fibers 11.

Once the fiber bundle 10 is wound, both ends of the fibers 11 are firmly potted in potting material, such as polyurethane or silicone, and a slice of the potting material containing the fibers is removed at both ends to expose the lumens 12 of fibers. The potted bundle is then positioned within an oxygenator housing so that a single gas source can simultaneously supply all the fibers 11, which are manifolded at the ends. As the blood flows over outside and oxygen flows inside of the fibers 11, the blood exchanges carbon dioxide for oxygen across the microporous membrane.

As a result of this bundle 10 configuration it is possible to contain a large membrane surface area in a compact volume. In other words, the wall of each individual fiber 11 cumulatively adds to the gas exchange surface area.

Figure 2:
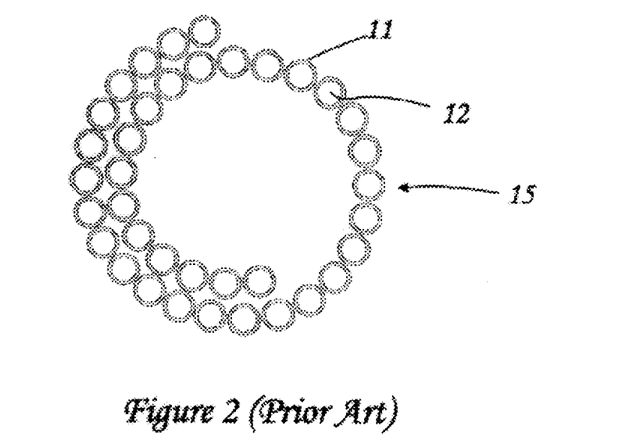
FIG. 2 is enlarged diagrammatic illustration of a prior art MMHF membrane where the fibers are spirally wound and undimentionally oriented.
Figure 3:
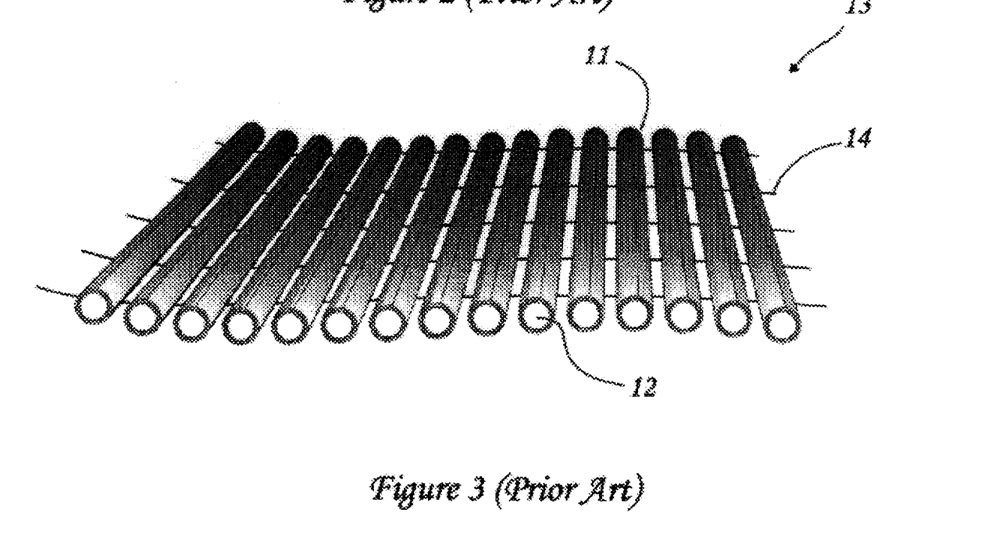
FIG. 3 is a diagrammatic illustration of a prior art membrane where individual fibers are maintained at evenly spaced intervals.

Several manufacturers have also begun providing MMHFs in a sheet-like form 13 exhibiting even spacing among the fibers 11. Weaving filaments 14, typically Dacron®, maintain the proper spacing but do not contribute to the gas exchange surface area. This is generally illustrated in FIG. 3. Forming a bundle with this spaced sheet results in adjacent fibers in the same layer not touching one another. The design is useful because it minimizes the regions where the fibers 11 can separate apart, thus maintaining a uniform blood flow throughout the entire fiber bundle. These arrays are typically spirally wound into bundles 15, as seen in FIG. 2, and potted at both ends as previously mentioned.

When used for extended periods of time, MMHF based oxygenators have been known to suffer from plasma leakage. Plasma leakage is generally a time dependent situation where blood plasma eventually leaks through the pores of the MMHF rendering its gas exchange capabilities completely ineffective. While not as often a problem in certain situations, plasma leakage can occur in short term procedures, i.e. in CPB surgery.

In an effort to ameliorate the problem of plasma leakage, a multilayered, composite MMHF, containing a polyurethane inner layer sandwiched between two microporous polyethylene supporting layers, has emerged. Similarly, a polypropylene MMHF coated with heparin bonded silicone, for an intravenous oxygenator (IVOX), has been proposed in the scientific literature. Gas transfer through these composite membranes, however, is obviously more limited in comparison to the microporous membrane alone, because the gas must diffuse through both the solid membrane and the microporous membrane. The tradeoff for reduced plasma leakage is therefore reduced gas transfer.

To further alleviate the plasma leakage problems of MMHF oxygenators, spirally wound solid silicone membrane oxygenators are typically used in long term applications. Being solid, these members do not have the same propensity for plasma leakage. The solid silicone membrane oxygenators do, however, require almost twice the surface area to achieve the same gas exchange capabilities as microporous hollow fibers. This is not because the membranes are solid, but rather because of the lack of convective mixing over the relatively flat solid silicone membrane in comparison to that achievable over a bundle of a thousand hollow fibers. The oxygenated blood boundary layer and not the membrane itself presents the major obstacle to oxygen diffusion to the blood.

Another potential problem associated with using MMHFs is that the gas side pressure of the system must always be below the blood slide pressure in order to prevent gas embolization, the potentially fatal consequences of which are well documented. If the gas pressure is higher than the blood pressure, gas can freely travel through the micropores into the blood. Embolization can also occur when the gas outlet port becomes occluded or damped, or if water condensation accumulates inside the lumen of the fibers thus plugging the exhaust of oxygen and carbon dioxide.

To reduce the risk of gas embolization, manufacturers of integrated systems have mounted the oxygenators below the venous reservoir, maintaining the blood side pressure at least above atmospheric pressure. Solely mounting the oxygenator below the venous reservoirs may not impede some modes of gas embolization since the typical oxygen supply line is regulated at 50 psi (2500 mmHg) whereas the maximum blood side pressure in the oxygenator is typically below 700 mmHg.

Thus the compactness, uniformity, and effectiveness of MMHFs and the ability to withstand plasma leakage and gas embolization of solid membranes, are desirable properties in a membrane designed blood oxygenation.

In view of the foregoing limitations and shortcomings of the prior art technology, as well as other disadvantages not specifically mentioned above, it should be apparent that there still exists a need in the art for an improved gas permeation membrane.

It is therefore a primary object of this invention to fulfill that need by providing a hollow fiber membrane exhibiting high gas permeation characteristics.

Another object of this invention is to provide a hollow fiber membrane of uniform construction which lends itself to compact designs in gas permeation devices.

It is also an object of the present invention to provide a membrane having an increased gas exchange surface area per volume over previously known constructions.

A further object of this invention is to provide a hollow fiber membrane which is not susceptible to plasma leakage and which exhibits low hemolysis in a blood oxygenation application.

Yet another object of this invention is to provide a method for manufacturing a hollow, solid wall fiber membrane meeting the above objects.

SUMMARY OF THE INVENTION

In trying to achieve the above and other objects, the present inventor was prompted to concentrate on designing a membrane with a fiber geometry that exhibited enhanced convective mixing for efficient gas exchange and compactness. In so doing, the concept of a multi-dimensional, hollow fiber array membrane presented herein was arrived at. The membrane allows for uniform mixing, and unlimited flexibility in design parameters. Generally, a membrane according to the principles of the present invention includes a series of hollow fibers which are angularly oriented so as to intersect one another. The orientation can be criss-crossed (at any angle) to define a two-dimensional membrane or a three-dimensional membrane. By intersecting the fibers, the orientation results in the establishment of open areas between laterally adjacent fibers and this results in the downstream fibers being located in a highly mixed flow or wake generated by the upstream fibers. A passageway is defined interiorly of each fiber and, as a result of the intersection of the fibers, the passageways of the various fibers intersect and are in communication with one another.

An additional aspect of the present invention is the method by which the membrane is constructed. In constructing the membrane, a mesh or matrix of intersecting stands is first provided. The strands of the mesh are oriented relative to one another to intersect and defining open areas between laterally adjacent fibers. The mesh is then coated with a second material that forms a layer over the mesh. Any second material located in the open areas between laterally adjacent fibers is removed so that these areas remain open.

Once the mesh has been coated with this second outer layer, a plurality of passageways are formed interiorly of the outer layer. At least some of these passageways are oriented relative to one another so that the passageways intersect and are in communication with each other. As more fully described below, various methods can be utilized to provide the mesh, to provide the outer coating over the mesh and to form the passageways within the outer coating.

A further aspect of the invention is an apparatus which incorporates the membrane described above in order to achieve gas permeation into a fluid. One variety of such devices are blood oxygenators. The invention will also find utility as a heat exchanger for extracorporeal circulation and dializer for dialysis.

In these devices, the membrane of the present invention is wound, rolled or otherwise formed into a membrane bundle having opposed ends. The ends are potted in a housing and this seals the respective ends in communication with a first fluid inlet and a first fluid outlet of the housing. This results in one entire end of the bundle being manifolded with the first fluid inlet of the housing. This is similarly done with the outlet end of the bundle and a first fluid outlet of the housing. In addition to the first fluid inlet and outlets, the housing is provided with a second fluid inlet and outlet. The second fluid inlet and outlet allow a second fluid to flow over the exterior surfaces of the bundle, through the various openings between intersecting individual fibers, and out through the second fluid outlet. With the first fluid flowing through the interior of the bundle and the second fluid flowing over the exterior of the bundle or vice versa, the first fluid (for example, oxygen) permeates through the solid wall member and into the second fluid (for example, blood).

Various types of materials can be used to form the fibers of the membrane of the present invention. Two examples of materials are silicone and polyurethane and the walls of the fibers may be alternatively solid or microporous.

When a solid wall material is used to define the fibers of the membrane, an oxygenator according to the principles of the present invention exhibits gas transfer characteristics which are comparable with the above mentioned MMHF devices while eliminating plasma leakage. It is believed that the high gas transfer characteristics are achieved because the membrane of the present invention has approximately twice the surface area (per unit volume) as an MMHF exhibiting the prior parallel fibers. Furthermore, with the present membrane an increase in downstream convective mixing is expected due to the mixed flow created as a result of the multi-dimensional array.

Additional benefits and advantages of the present invention will become apparent to those skilled in the art to which the present invention relates from the subsequent description of the preferred embodiment and the appended claims, taken in conjunction with the accompanying drawings.

DETAILED DESCRIPTION OF THE INVENTION

Figure 4:
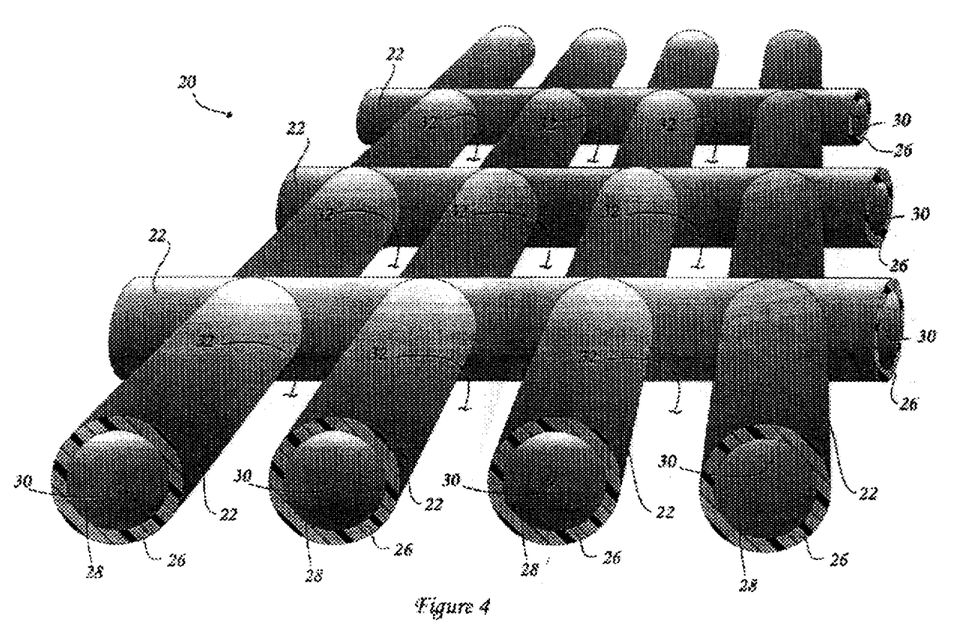
FIG. 4 is an enlarged, perspective illustration of one embodiment of a membrane according to the principles of the present invention.
Figure 7:
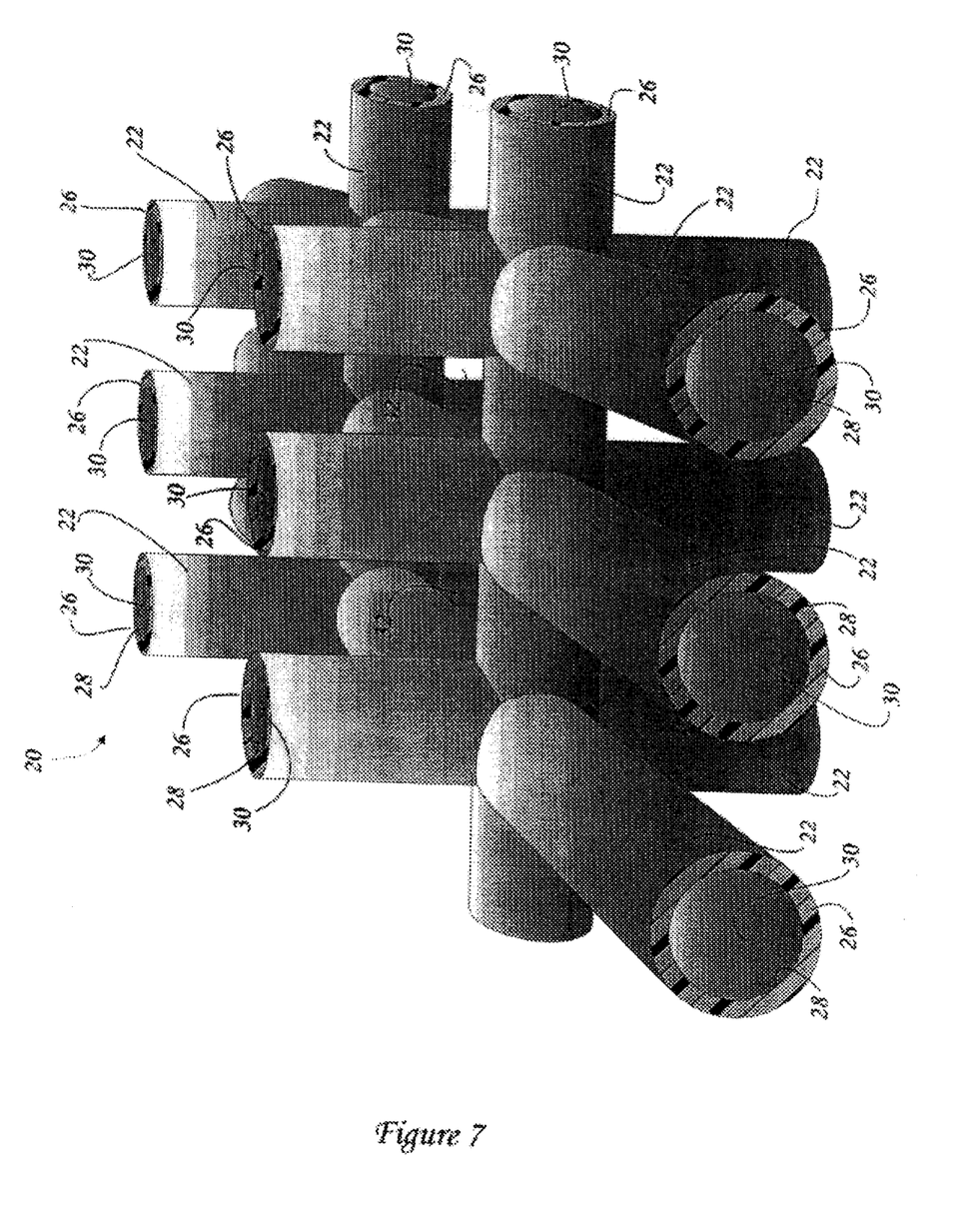
FIG. 7 is an enlarged, perspective illustration of one embodiment of a membrane according to the principles of the present invention.

Referring now in detail to the drawings, there is shown in FIG. 4 a greatly enlarged perspective view of a portion of a membrane, generally designated at 20, embodying the principles of the present invention. The membrane 20 includes a series of hollow stands or fibers 22 interconnected with one another so as to form the multidimensional array. While FIG. 4 illustrates a portion of a two-dimensional array embodiment of the present invention, FIG. 7 illustrates a portion of a three-dimensional array embodiment. Herein the two-dimensional embodiment will be described in greatest detail with it being understood that the description is generally equally applicable to the three-dimensional embodiment as well.

Each fiber 22 has a side wall 26 whose interior surfaces 28 defines a passageway 30 through the fiber 22. Individual ones of the fibers 22 are oriented relative to one another such that their passageways 30 intersect to permit communication therebetween. As seen in FIG. 4, the passageways 30 can intersect at generally right angles relative to one another, but the angle between intersecting fibers 22 can be any desired angle. As such, the angle can be 90°, greater than 90°, or less than 90°.

Because of the intersecting of the fibers 22, open areas 32 are generally defined between adjacent fibers 22. These open areas 32 permit the flow of fluid over, between and around the array of fibers 22 as more fully described below.

Referring now to FIGS. 5a–5e, a method of constructing a membrane 20 embodying the principles of the present invention will be discussed. Alternate and varying methods are also referred to and will be readily appreciated by one skilled in the art.

Figures 5A, 5C:
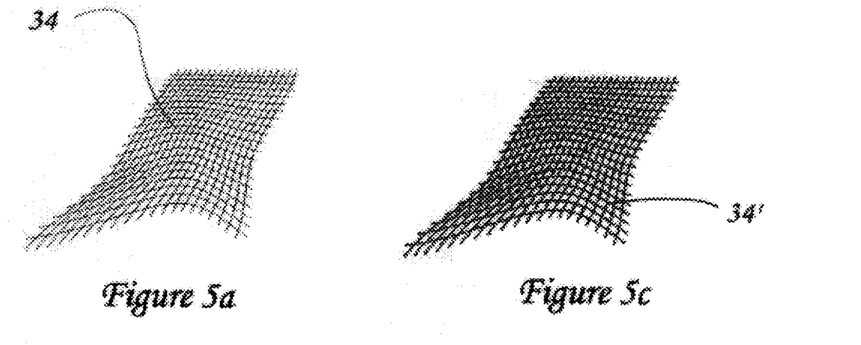
FIGS. 5a–5e are a diagrammatic illustration of a method of constructing a membrane according to the principles of the present invention.

The first step in constructing the membrane 20 involves the formation of a uniform mesh, netting or screen 34 with the open areas 32 mentioned above. The screen 34 preferably is formed of a material, such as polyvinyl alcohol (PVA), with individual stands 36 having a diameter of about 0.010 to 0.015 inches, it being understood that diameters greater or less than this range would also be possible, depending on the particular application of the membrane 20.

PVA material is preferable for the screen 34 since it is a non-toxic, water soluble and environmentally safe polymer that can be engineered to dissolve in water or steam at a desired temperature, which is desirable for reasons more fully set out below. The screen 34 itself can be manufactured by any well known method including, but not limited to, molding, extruding, stamping (of rectangular or rounded openings), weaving or other suitable techniques. In addition, the screen 34 can be initially manufactured with unlimited variations in its design parameters (strand or passageway diameter or shape, vertical and horizontal spacing, etc.) such that specific gas exchange applications can be more precisely accommodated.

Figure 5B:
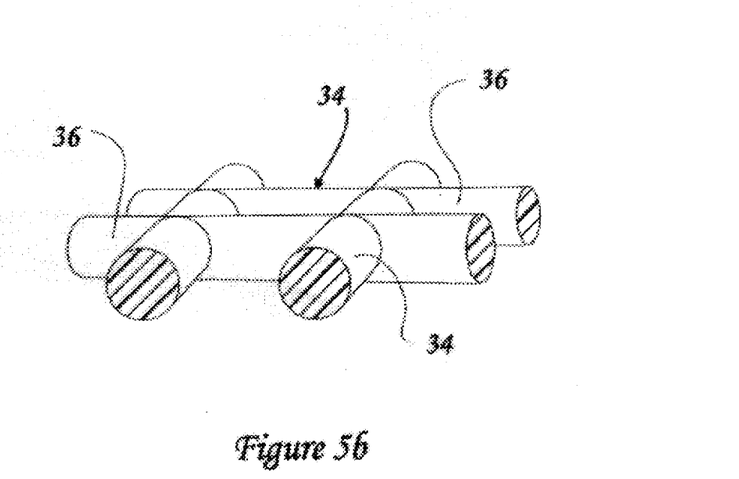

A second material is next applied over the screen 34 to form a coated screen 34' having a thin layer or coating 38 over the surface of the underlying screen 34. The coating 38 can be any one of a variety of materials so long as it is compatible with the fluids with which the membrane 20 will be used and so long as the material forms a gas permeable coating or wall about the underlying screen 34. Preferably, the wall is a solid wall in those situations where plasma leakage is a concern. As the term is used herein, "solid wall" means the wall formed by the coating 38 is not porous or microporous as those terms are commonly understood in the field of this invention. In other situations the wall might be microporous. In still further situations, the wall might be a composite or combination of the above having both a microporous layer and a solid layer.

One preferred method of applying the coating 38 is to dip-coat the screen 34 in a dispersion of the second material, for example a medical grade silicone (such as Silastic™, commercially available from Dow Corning of Midland, Mich.) when forming a solid wall membrane or other material. The ratio of solvent to silicone in the dispersion determines the viscosity of the dispersion and the thickness of the coating 38 deposited on the underlying screen 34. Accordingly, dip-coating can result in a very thin or thick coating 38 of the second material being deposited on the surface of the screen 34. Care is taken to prevent any of the coating material from forming a web across the open areas 32 between the individual strands 36 of the screen 34. One way to prevent web formation is by gently blowing or forcing air across the coated screen 34' or subjecting the coated screen 34' to a vacuuming. The coated screen 34' can also be rotated while the solvent evaporates and the silicone solidifies to ensure a uniform coating 38 thickness about the screen 34 and minimal webs. An alternative method of applying the coating 38 to the screen 34 is to apply the dispersion by spraying coating. A coating 38 thickness of about 0.002 inches is preferred for blood oxygenation applications and multiple dip or spray layers may be necessary to achieve such a coating thickness. A greater or lesser thickness could be utilized as dictated by the specific application.

Once the outer layer or coating 38 has solidified, the passageways 30 are formed within the coating 38. In the PVA-silicone embodiment, the coated screen 34' is subject to water vapor, for example steam at about 250° F. Since water vapor is highly permeable through silicone ($3000 \times cc \times cm/cm \ 10^{-9} \ cc \times cm/cm^2/sec/mmHg$) and is sixty times more permeable than oxygen, the water vapor readily permeates through the outer coating 38 of silicone. As a result, the water soluble PVA screen 34 dissolves and the dissolved PVA is purged from within the coating 38. The result is the formation of the membrane 20 with its two-dimensional, hollow array. Purging can be achieved by blowing with a pressurized fluid (such as steam), by centriguation, by a combination of the two, or other methods. Gas (such as oxygen) can therefore flow within the passageway 30 of the membrane 20, as designated by arrows 40, while a second fluid (such as blood) is provided to flow over the exterior of the membrane 20, as designated by arrows 42, or vice-versa.

Figure 5D:
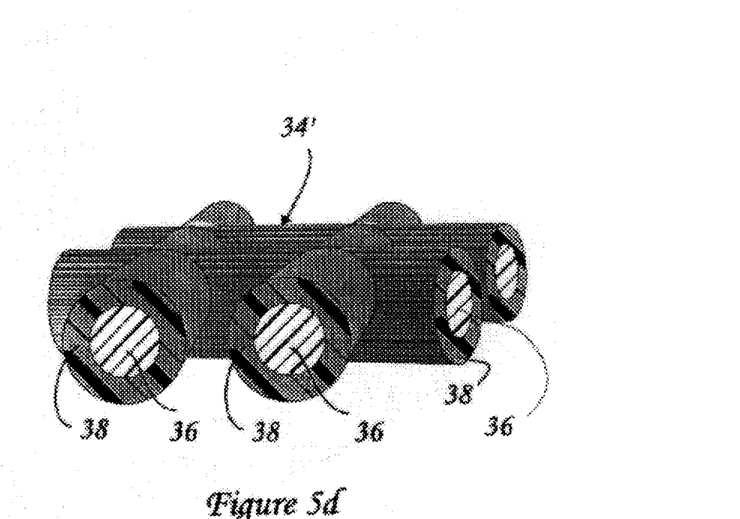
Figure 5E:
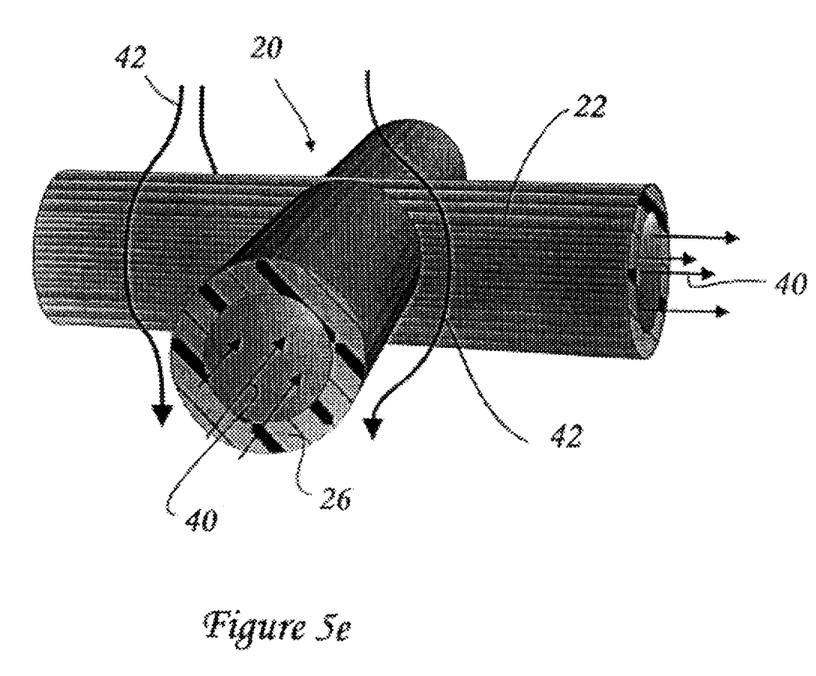

In the practice of manufacturing an oxygenator or other gas exchange device, the coated screen 34' may be provided to a device manufacturer prior to removal of the inner screen 34 and the formation of the passageways 30 within the outer coating 38. The coated screen 34' can therefore be provided in a sheet or roll form, having the required width (e.g. approximately six inches for an oxygenator), on a spool with the necessary length to achieve the desired gas exchange surface area (e.g. 2 $m^2$ for oxygenators) being utilized from the spool. The coated screen 34' is then folded or wound, spirally or otherwise, to create a fiber bundle 44. The bundle 44 is supported as the ends of the bundle 44 are potted in a suitable potting material 46 by conventional potting techniques, typically centrifugation. Once the bundle 44 is potted, the coating 38 and underlying screen 34 can be exposed by slicing off a portion of the potted ends 46. The fiber bundle 44 is next exposed to a steam that will dissolve and flush the PVA screen 34 from the coating 38 leaving the hollow fiber membrane 20.

With the above method, the passageways 30 are not formed until after the bundle 44 has been potted. This is preferred in that the screen 34 provides internal support to the outer coating 38 during the potting. Furthermore, the screen 34 provide an internal and temporary plug that will prevent the potting material 46 from entering into the passageways 38 of the membrane 20 during centrifugation. Alternatively, the membrane 20 can be provided with the underlying screen 34 already removed or without the coating yet applied.

In an alternative method of constructing the oxygenator, the underlying mesh is wound, potted and positioned in the housing. The mesh is then coated by filling the housing with the coating material and draining the excess material. By subjecting the housing to a vacuum, the coating material is prevented from forming web formations in the interstitial openings.

Still alternative methods would vary the order of the above steps.

The resulting membrane 20 is effectively a two-dimensional array of interconnected, hollow walled fibers 22 that allows for gas flow in two dimensions and permeation through the walls. The currently used solid and microporous hollow fibers only permit the internal flow of a gas in a single, axial direction of the fibers. The present invention also maintains fiber 22 separation or spacing while providing the above two-dimensional array with a 100% gas permeable construction.

If the X and Y screen spacing used in the present invention is the same as that used between parallel fibers in the prior art membrane of FIG. 1, then the membrane 20 of the present invention will exhibit close to twice the surface area per unit volume occupied by the prior art membrane and will exhibit an increased convective mixing at downstream locations in the bundle 44 due to the wake generated by the multi-dimensional array. As a result of the above two properties, the present membrane requires less bundle volume than previously required to achieve the same gas exchange, all while minimizing contact between the blood and the non-biological surfaces of the membrane 10.

In addition to the above methods of forming the passageways 30 in the coated screens 34', it should be noted that the passageways 30 can be formed from any alternative method that will allow for fluid flow within the membrane 20 to occur. Thus, the screen 34 may be completely removed, partially remain in an altered (chemically, physically, or thermally), shrunk or be otherwise modified in a way which renders the screen 34 porous. Additionally, the screen 34 can be coated with another intermediate substance, prior to coating with the outer layer, so long as the intermediate substance will permit gas exchange or flow thereacross. The intermediate material may therefore be of any material that is gas permeable, microporous, solid or otherwise.

Figure 6A:
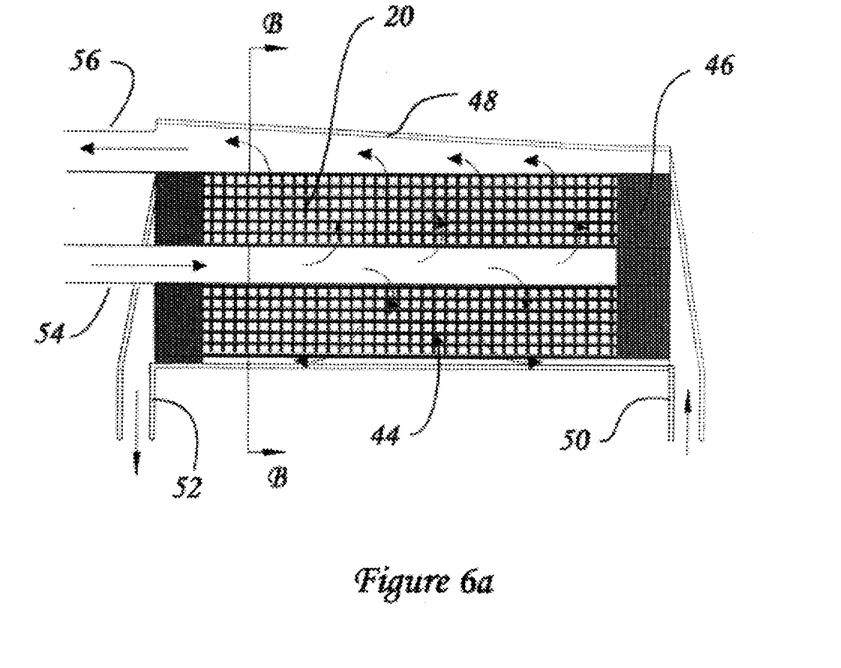
FIGS. 6a and 6b are sectional views of an oxygenator incorporating the principles of the present invention.
Figure 6B:
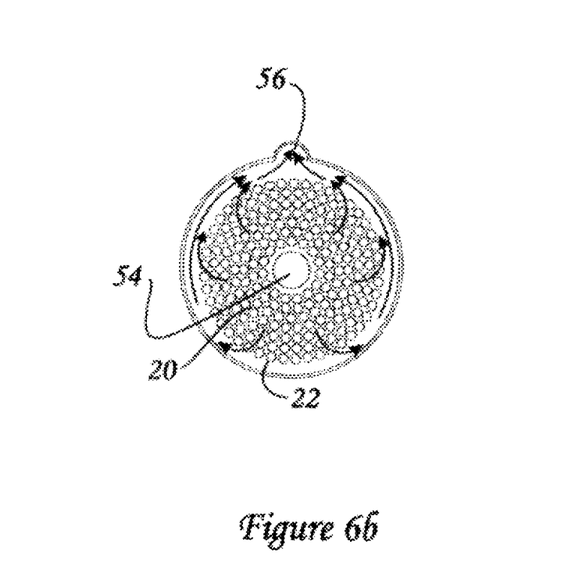

After the above bundle 44 has been formed, it is then enclosed within a housing 48 having a gas inlet 50 and outlet 52 in communication with the ends of the bundle 44 to manifold gas to all the exposed passageways 30 within the fibers 22. The housing will also include a second fluid inlet 54 and outlet 56 which are located to flow a second fluid over the exterior surfaces of the membrane 20.

While the above description constitutes the preferred embodiment of the present invention, it will be appreciated that the invention is susceptible to modification, variation and change without departing from the proper scope and fair meaning of the accompanying claims.

I claim:

1. A gas permeable membrane comprising:
a plurality of unitarily formed conduit members, said conduit members each having walls defining an interior surface and a passageway through said conduit member, said conduit members being angularly oriented to intersect one another such that said passageways of said conduit members also intersect and communicate with one another thereby forming a multi-dimensional array membrane.

2. A membrane as set forth in claim 1 wherein said conduit members form a two-dimensional array membrane.

3. A membrane as set forth in claim 1 wherein said conduit members form a three-dimensional array membrane.

4. A membrane as set forth in claim 1 wherein said conduit members intersect at right angles.

5. A membrane as set forth in claim 1 wherein said plurality of conduit members includes a first set of said conduit members extending in a first direction, a second set of said conduit members extending in a second direction.

6. A membrane as set forth in claim 5 wherein said first set of said conduit members intersect said second set of conduit members at right angles.

7. A membrane as set forth in claim 5 wherein said plurality of conduit members also includes a third set of said conduit members.

8. A membrane as set forth in claim 7 wherein said third set of said conduit members intersect said first set of said conduit members.

9. A membrane as set forth in claim 7 wherein said third set of said conduit members intersect said first and said second sets of said conduit members.

10. A membrane as set forth in claim 9 wherein said first, said second and said third sets intersect at a common intersection point.

11. A membrane as set forth in claim 9 wherein said first, said second and said third sets intersect at right angles.

12. A membrane as set forth in claim 1 wherein said membrane is silicone.

13. A membrane as set forth in claim 1 wherein said walls of said conduit members have a thickness of approximately 0.002 inches.

14. A membrane as set forth in claim 1 wherein said passageways have a diameter in the range of 0.010 to 0.015 inches.

15. A membrane as set forth in claim 1 wherein said membrane is permeable to water vapor.

16. A membrane as set forth in claim 1 wherein walls of said conduit members are solid.

17. A membrane as set forth in claim 1 wherein walls of said conduit members are microporous.

18. An apparatus for permeating a first fluid into a second fluid, said apparatus comprising:
a housing defining a central cavity and having a first fluid inlet and a first fluid outlet, said housing also having a second fluid inlet and a second fluid outlet;
a membrane having a plurality of hollow fibers, said fibers being unitarily formed with one another and intersecting to define open areas therebetween, said fibers intersecting such that passageways through said fibers are in communication with one another thereby defining a multi-dimensional array membrane;

a fiber bundle formed of said membrane and having opposing ends in communication with one another through said passageways, said fiber bundle being positioned in said housing;

sealing means for sealing said opposing ends of said fiber bundle within said housing with said first fluid inlet being in communication with one end of said fiber bundle and said first fluid outlet being in communication with another end of said fiber bundle, said sealing means cooperating with said housing to define a second fluid passageway between an exterior surface of said membrane, an interior surface of said housing and from said second fluid inlet to said second fluid outlet; and whereby the second fluid flows from said second fluid inlet about said exterior surface of said membrane and through said open areas to said second fluid outlet as said first fluid flows through said passageways within said fibers and whereby the first fluid permeates through said walls of said fibers and into the second fluid.

19. An apparatus as set forth in claim 18 wherein said fibers are oriented in a three-dimensional array.

20. An apparatus as set forth in claim 18 wherein said fibers are oriented in a two-dimensional array.

21. An apparatus as set forth in claim 18 wherein said membrane is in a sheet form.

22. An apparatus as set forth in claim 21 wherein said membrane is wound to form said fiber bundle.

23. An apparatus as set forth in claim 21 wherein said membrane is spirally wound to form said fiber bundle.

24. An apparatus as set forth in claim 18 wherein said fibers have solid walls.

25. An apparatus as set forth in claim 18 wherein said fibers have microporous walls.

26. A method of manufacturing a gas permeable membrane for permeating a first fluid into a second fluid, said method comprising the steps of:

forming a mesh of a first material, said mesh including a plurality of strands oriented so as to intersect one another and so as to define open areas between adjacent strands;

coating said mesh with an outer layer of a second material to form a coated mesh, the second material being gas permeable to the first fluid;

preventing the second material from obstructing the open areas between adjacent strands such that the open areas remain open after said coating step; and forming a plurality of passageways interiorly of the outer layer with at least some of the passageways being oriented to intersect one another and communicate with one another.

27. The method as set forth in claim 26 wherein the step of forming the passageways includes the step of removing the first material from within the outer layer of the second material to form a membrane of hollow fibers.

28. The method as set forth in claim 27 wherein said removing step includes the steps of dissolving the mesh and purging the dissolved mesh from within the outer layer.

29. The method as set forth in claim 28 wherein said removing step further includes the step of removing the outer layer from at least one end of the mesh.

30. The method as set forth in claim 28 wherein said dissolving step involves permeating a fluid through the outer layer.

31. The method as set forth in claim 30 wherein the fluid includes water vapor.

32. The method as set forth in claim 26 wherein the outer layer is dip-coated onto the mesh.

33. The method as set forth in claim 26 wherein the outer layer is sprayed onto the mesh.

34. The method as set forth in claim 26 wherein the mesh is formed by one of the following: molding, extruding, stamping or weaving.

35. The method as set forth in claim 26 further comprising the steps of forming said mesh into a fiber bundle, positioning the fiber bundle in a housing having first and second fluid inlets and first and second fluid outlets, and sealing the fiber bundle within the housing.

* * * * *